United States Patent
Colin et al.

(10) Patent No.: US 8,104,329 B2
(45) Date of Patent: Jan. 31, 2012

(54) METHOD AND INSTALLATION FOR DETERMINING RHEOLOGICAL CHARACTERISTICS OF A FLUID, AND CORRESPONDING IDENTIFYING METHOD

(75) Inventors: Annie Colin, Bordeaux (FR); Galder Cristobal, Singapore (SG); Pierre Guillot, Pessac (FR); Mathieu Joanicot, Chatenay Malabry (FR)

(73) Assignees: Rhodia Chimie, Aubervilliers (FR); Centre National de la Recherche Scientifique (C.N.R.S.), Paris (FR)

( * ) Notice: Subject to any disclaimer, the term of this patent is extended or adjusted under 35 U.S.C. 154(b) by 495 days.

(21) Appl. No.: 11/792,511

(22) PCT Filed: Dec. 9, 2005

(86) PCT No.: PCT/FR2005/003094
§ 371 (c)(1),
(2), (4) Date: Feb. 20, 2008

(87) PCT Pub. No.: WO2006/061524
PCT Pub. Date: Jun. 15, 2006

(65) Prior Publication Data
US 2009/0038379 A1   Feb. 12, 2009

(30) Foreign Application Priority Data

Dec. 10, 2004   (FR) ..................................... 04 13191

(51) Int. Cl.
*G01N 11/00* (2006.01)

(52) U.S. Cl. ..................................................... 73/54.01
(58) Field of Classification Search .................. 73/54.01
See application file for complete search history.

(56) References Cited

U.S. PATENT DOCUMENTS

| 3,808,877 A | 5/1974 | Blair |
| 4,884,437 A * | 12/1989 | Constant et al. ............. 73/54.01 |
| 5,327,778 A | 7/1994 | Park |
| 5,447,440 A | 9/1995 | Davis et al. |

FOREIGN PATENT DOCUMENTS

| WO | WO 02/39090 A2 | 5/2002 |
| WO | WO 03/008936 A2 | 1/2003 |

OTHER PUBLICATIONS

International Search Report corresponding to PCT/FR 2005/003094, issued on Mar. 14, 2006, 3 pages.
French Search Report corresponding to FR 0413191, issued on Aug. 10, 2005, 2 pages.

* cited by examiner

*Primary Examiner* — Hezron E Williams
*Assistant Examiner* — Rodney T Frank
(74) *Attorney, Agent, or Firm* — Buchanan Ingersoll & Rooney, P.C.

(57) ABSTRACT

The method comprises:
causing a reference fluid ($F_2$) having known rheological characteristics, and an unknown fluid ($F_1$) to flow in parallel in a microchannel (126);
identifying at least one data item representative of the interface (I) between these fluids in the parallel flow, and in particular the position of said interface; and
determining the rheological characteristics of the unknown fluid, from the or each identified data item.

33 Claims, 8 Drawing Sheets

METHOD AND INSTALLATION FOR DETERMINING RHEOLOGICAL CHARACTERISTICS OF A FLUID, AND CORRESPONDING IDENTIFYING METHOD

CROSS REFERENCE TO PRIORITY APPLICATIONS

This application is the United States national phase of International Application No. PCT/FR 2005/003094, filed Dec. 9, 2005, published in French as International Publication No. WO 2006/061524 A1 on Jun. 15, 2006, and claims priority of French Application No. 0413191, filed Dec. 10, 2004, each hereby expressly incorporated by reference in its entirety and each assigned to the assignee hereof.

The present invention relates to a method and to an installation for determining rheological characteristics of a fluid, and it also relates to a method of identification that makes use of the method and/or the installation.

There exist numerous fluids that are encountered in daily life and that can be processed by the invention. Purely by way of indication, mention can be made in particular of foams, emulsions such as mayonnaise, or indeed concentrated wetting agents such as shampoos. These fluids are generally obtained by mixing various components, such as for example oil, water, wetting agents, polymers, or indeed alcohols.

Under such conditions, a formulating engineer needs to develop a formula that is active, e.g. for washing if it is a shampoo, but that is also stable over time, easy to handle, and that possesses a texture that is agreeable to the consumer. For this purpose, it is necessary to have control over the rheological properties of such formulations, in order to be capable of adjusting them. These properties are of great importance, given that they have direct repercussions on manufacturing methods, on pumping, and on mixing the fluids in question.

As is well known, with a simple fluid, such as water, viscosity is independent of the shear rate applied to the fluid. The fluid is then said to be Newtonian.

Things are quite different for complex fluids that are characterized by the existence of a scale size that is intermediate between the size of a molecule and the size of a sample. By way of example, this scale size can be the size of drops in an emulsion, or the size of bubbles in a foam.

Such complex fluids, which are said to be non-Newtonian, possess viscosity that is liable to vary when the applied stress increases. The rheological response of such fluids is therefore not a single viscosity coefficient, but a response curve referred to as a flow curve. A flow curve shows how stress varies as a function of shear rate, the local slope of the curve being the viscosity that corresponds to the shear rate in question.

In order to adjust the viscosity of a formulation, it is common practice to add thickeners, e.g. polymer solutions or salts, or even jelling agents, e.g. polymers or proteins. In order to determine this viscosity value accurately, various mixtures of varying compositions are usually prepared. Their mechanical properties are then measured using an appropriate apparatus, known as a rheometer.

One such rheometer is sold for example by the supplier TA Instruments, under the trade reference AR 1000 N. It comprises two coaxial cylinders, defining an intermediate space that receives the fluid whose rheological properties are to be determined.

Mechanical torque is then applied to the inner cylinder by means of a motor. Under such conditions, it is the speed of rotation of the axis of the motor that is measured, it being understood that the higher this speed, the less the fluid is considered to be viscous.

Nevertheless, implementing such a rheometer implies certain drawbacks.

Firstly, it leads to a high level of fluid consumption, since each measurement makes use of a non-negligible quantity of components, typically lying in the range 5 cubic centimeters ($cm^3$) to 30 $cm^3$. Furthermore, that rheometer is relatively time-consuming to handle, since each measurement requires a corresponding preparation of the sample for testing.

Furthermore, and in general, there exists a constant need in industry to develop new products, presenting new properties, e.g. new chemical compounds or new compositions including new chemical substances and/or new associations of chemical substances. The rheology of substances is a property that is important in a large number of applications, and it is often necessary to test it during the research and development process. There is a need for methods and installations that enable the research and development process to be accelerated, e.g. in order to test a large number of substances and/or to implement tests on smaller quantities of those substances, and/or to implement tests more quickly.

That said, the invention seeks to remedy the various above-mentioned drawbacks of the prior art, and/or to satisfy the above-mentioned need.

The invention seeks in particular to implement a method enabling the rheological characteristics of a fluid to be determined while using a very small quantity of the fluid. In particular, the invention seeks to provide such a method that makes it possible to have access to the same properties as when using a state of the art rheometer.

The invention also seeks to propose an installation enabling the method to be implemented, which installation is compact and of simple structure, while making use of a small amount of external equipment.

To this end, the invention provides a method of determining rheological characteristics of an unknown fluid, the method comprising the following steps:
  causing both a reference fluid having known rheological characteristics and said unknown fluid of rheological characteristics that are to be determined to flow in parallel in a flow microchannel;
  identifying at least one item of data representative of an interface between said two fluids in said parallel flow; and
  determining the rheological characteristics of the unknown fluid from the or each identified item of data.

The invention also provides an installation for implementing the method as defined above, the installation comprising a device for determining rheological characteristics of the unknown fluid, the determination device comprising:
  a body, in particular forming a plate;
  a flow microchannel formed in the body and suitable for receiving the parallel flow of the unknown fluid and of the reference fluid;
  means for introducing said two fluids into the flow microchannel;
  means for identifying at least one item of data representative of the interface between said two fluids in the parallel flow; and
  means for determining rheological characteristics of the unknown fluid, from the or each identified data item.

Finally, the invention provides a method of identifying chemical compounds, associations of chemical compounds, or compositions, in particular those that present rheological properties of interest, the method comprising the following steps:

a) preparing at least two different compounds, associations, or compositions;

b) measuring at least one rheological characteristic by the method as defined above, and/or with the help of the installation as defined above; and c) identifying a compound, association, or composition presenting a rheological property of interest.

The invention is described below with reference to the accompanying drawings, given solely as non-limiting examples, in which.

Figure 1:
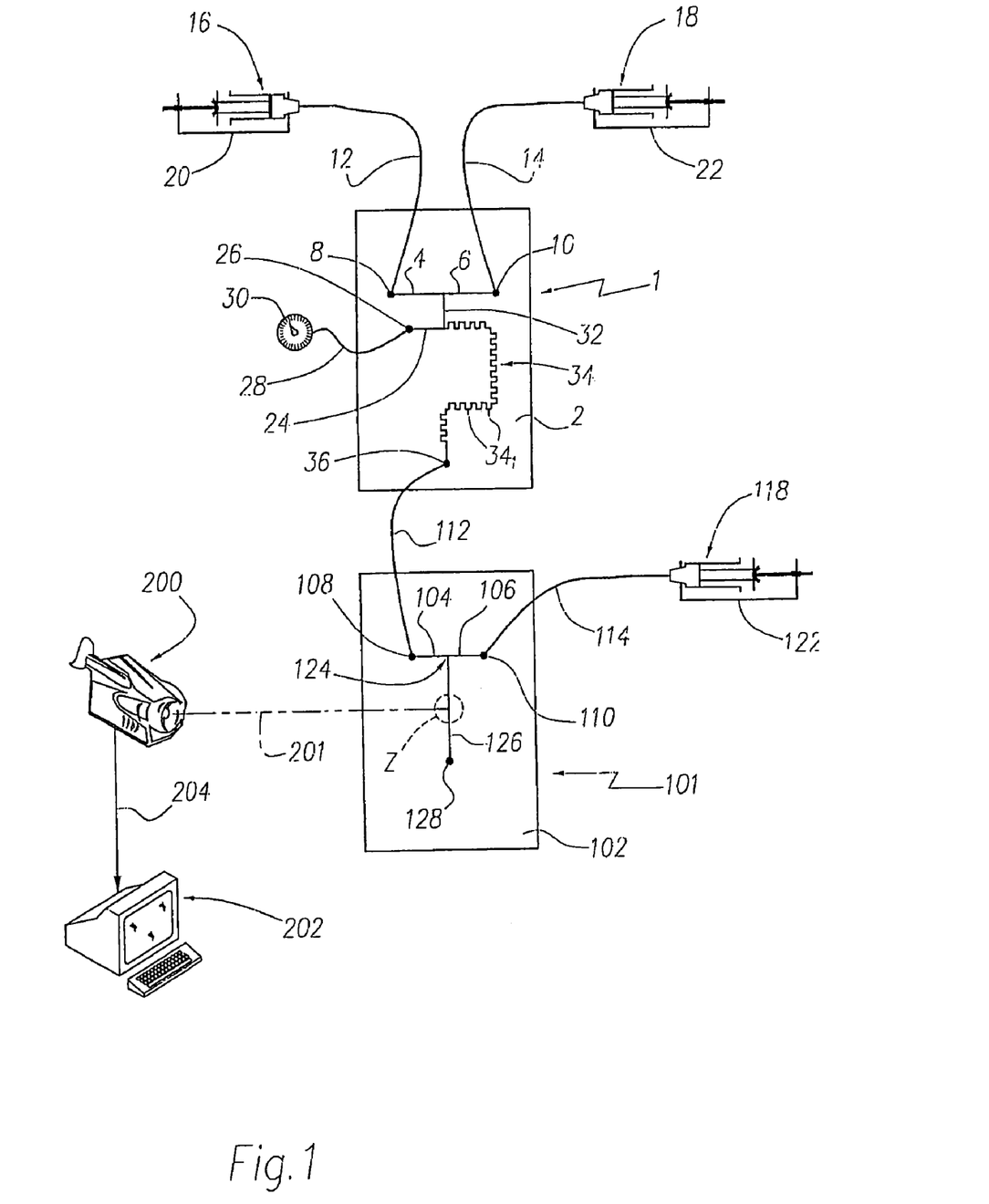
FIG. 1 is a diagrammatic face view showing an installation for determining the rheological characteristics of a fluid, which installation is in accordance with the invention.

The installation in accordance with the invention as shown in FIG. 1 comprises firstly a mixer device given overall reference 1. The device comprises a body 2 forming a plate that can be made in conventional manner out of poly(dimethylsiloxane), also known as PDMS.

The plate 2 has a typical length of 60 millimeters (mm), a typical width of 40 mm, and a typical thickness of 4 mm. It is etched with various microchannels using procedures that are conventional in the state of the art. In known manner, a plate of glass (not shown) is fitted, e.g. by adhesive, over the plate 2 of PDMS, so as to close the top faces of the microchannels.

The characteristic dimension of these microchannels, as involved in the invention, lies in the range about 10 micrometers (μm) to 1 mm, approximately. In typical manner, this dimension causes flow to be substantially laminar within the microchannels, with Reynolds' numbers of less than 1. As an indication, in order to illustrate the way in which the microchannels are made and the properties they have, mention is made of the work by Stéphane Colin, "Microfluidique" [Microfluidics], published by Editions Hermès Science Publications in "Traité EGEM série Microsystèmes".

More precisely, provision is made firstly for two microchannels 4 and 6 to feed two components, these microchannels extending horizontally in FIG. 1. Each microchannel is associated with an inlet 8 or 10 specific thereto for receiving a first end of a corresponding tube 12 or 14 whose other end is connected to a respective syringe 16 or 18. The flow rate of the component delivered by each syringe is controlled by a syringe pusher 20 or 22.

The plate 2 also has a microchannel 24 formed therein that enables a gas to be fed, e.g. air. In a manner analogous to that described above, this microchannel 24 is associated with an inlet 26, a tube 28, and a pressure gauge 30. The various mechanical members 8 to 22, and also 26 to 30, are of conventional type and are not described in greater detail below.

The two microchannels 4 and 6 meet initially at an intermediate microchannel 32, extending vertically in FIG. 1, itself put into communication with the microchannel 24. Downstream from this junction zone, there is thus formed a "mixer" microchannel 34. It should be observed that the microchannel 34 is provided with a succession of bends $34_1$ forming a zigzag configuration, with walls that constitute obstacles serving to mix the components, as described in greater detail below. The downstream end of the mixer microchannel 34 opens out into an outlet 36.

In addition to the mixer device 1, the installation of FIG. 1 also comprises an additional device 101 for determining the rheological characteristics of a fluid, as described below. This determination device 101 comprises firstly a plate 102 analogous to the above-described plate 2, having various microchannels etched therein, as described below. As for the mixer device 1, the plate 102 is made of PDMS and is associated with a glass plate (not shown) that serves to close the top portions of its microchannels.

The plate 102 has a first "upstream" microchannel 104 that extends horizontally in FIG. 1. The microchannel 104 is associated with an inlet 108 that is put into communication with the outlet 36 from the mixer device 1 via a tube 112.

A second upstream microchannel 106 is also provided, likewise extending horizontally, and associated with an inlet 110. This inlet is put into communication via a tube 114 with a syringe 118 delivering at a flow rate controlled by a syringe pusher 122.

It should be observed that a plurality of additional syringes could be provided, associated with corresponding syringe pushers, enabling other types of fluid to be delivered to the inlet 110, via the tube 114. Switching between such various syringes can be performed automatically. Control is provided by a computer, in conventional manner.

Figure 1A:
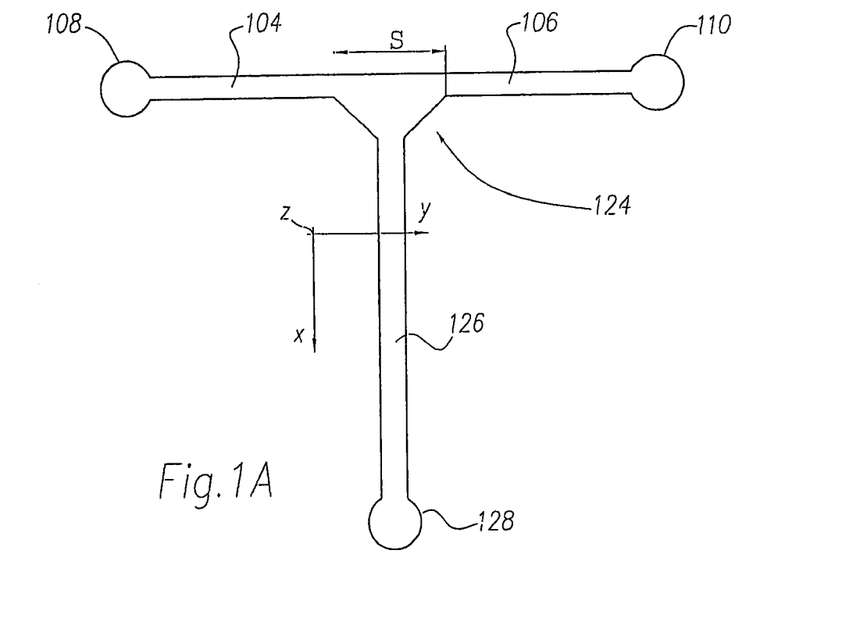
FIG. 1A is an enlarged face view showing more particularly a junction zone belonging to the FIG. 1 installation.

The two upstream microchannels 104 and 106 join in a junction zone 124 that is funnel-shaped, as can be seen more particularly in FIG. 1A. More precisely, the cross-section S of the zone 124 tapers downstream, i.e. going away from the two above-mentioned microchannels 104 and 106.

This junction zone 124 communicates with a microchannel 126 that is drawn vertically in FIG. 1, and referred to as a "flow" microchannel. At its downstream end, this flow microchannel is put into communication with an outlet 128, e.g. associated with a tube (not shown) serving to remove the effluents.

In accordance with the invention, the flow sections of the various microchannels 4, 6, 24, 32, 34, 104, 106, and 126 advantageously lies in the range 20 (μm) to 500 μm, and preferably in the range 50 μm to 200 μm.

The installation of the invention is also provided with a camera 200 connected to a computer 202 via a line 204. In conventional manner, the camera 200 is associated with a microscope, so that its beam 201 is suitable for viewing a zone of the flow microchannel 126. This zone, referred to as the "viewing" zone, is drawn in dashed lines in FIG. 1, where it is given the reference Z.

Operation of the above-described FIG. 1 installation is explained below.

In accordance with the invention, it is desired to determine rheological characteristics of an "unknown", fluid, in particular by optically reading the viewing zone Z. For this purpose, the unknown fluid is initially prepared by mixing two components in the mixer device 1.

The two components flow along the microchannels 4 and 6 at rates that are controlled by the syringe pushers 20 and 22. In this respect, a typical range of flow rates may be 1 microliter per hour (μL/h) to 100 milliliters per minute (mL/min).

Thereafter, these two components flow in the intermediate microchannel 32, presenting a flow that is generally parallel. It should be observed that in this microchannel 32, there is substantially no mixing between these two components, given the very nature of these microchannels, and in particular their very small section.

Furthermore, air is caused to flow in the microchannel 24 so as to create bubbles of gas. These bubbles generate disturbances in the parallel flow of the two components in the mixer microchannel 34. These disturbances are magnified by the microchannel 34 being provided with bends 34₁ that generate shocks in the above-mentioned flow.

Consequently, at the outlet 36, a well-mixed fluid is available having a composition that is accurately determined, given knowledge of the respective flow rates of the components delivered by the microchannels 4 and 6. In this respect, it should be emphasized that the composition of this unknown fluid can be modified in very simple manner, merely by varying said flow rates as delivered to the microchannels 4 and 6.

It should also be observed that using air in association with PDMS is advantageous. Given that PDMS is porous to air, the size of the bubbles tends to decrease as they advance along the mixer microchannel 34, with the air escaping progressively through the PDMS membrane.

Thus, by appropriately adjusting the air flow rate and the length of this microchannel, it is possible to obtain a fluid that is thoroughly mixed, while being substantially free from any bubbles of air. Consequently, subsequent determination of the rheological characteristics of the fluid is not disturbed by the presence of any gas.

In a variant, it is possible to associate a mixer gas and a material constituting the plate that are other than air and PDMS. By way of non-limiting example, mention can be made of helium, nitrogen, or indeed argon.

In a variant that is not shown, the number of components for mixing together in order to obtain the unknown fluid could be greater than 2. In this respect, the above-described mixing procedure is recommended with an additional component, either at the inlet to or at outlet from the mixer microchannel.

It should also be observed that the mixer device 1 need not be a bubble mixer. Under such circumstances, it could be constituted by any other device acting in known manner to increase the zone of contact between two miscible fluids. In non-limiting manner, particular mention can be made of having chevrons present in the channels, or indeed of creating pulses in the flows.

The unknown fluid, prepared in the mixer device 1, is then admitted to the inlet 108 of the microchannel 106 via the tube 112. Furthermore, a reference fluid having thoroughly known rheological characteristics is also caused to flow in the other upstream microchannel 106. These two fluids, respectively the unknown fluid and the reference fluid, then flow along the microchannel 126.

As mentioned above, flow within a microchannel is essentially of laminar type. Under such conditions, the two above-mentioned fluids flow in parallel within the microchannel 126. Nevertheless, it is advantageous to take certain precautions in order to ensure that this flow remains parallel.

For this purpose, when the fluids are miscible, the funnel shape of the junction zone 124 is advantageous. In addition, it is possible to add wetting agents to the reference fluid, thus encouraging said flow to be parallel, but without modifying the composition of the unknown fluid.

The description below begins with a first implementation of the invention for determining the rheological characteristics of the unknown fluid.

Figure 2:
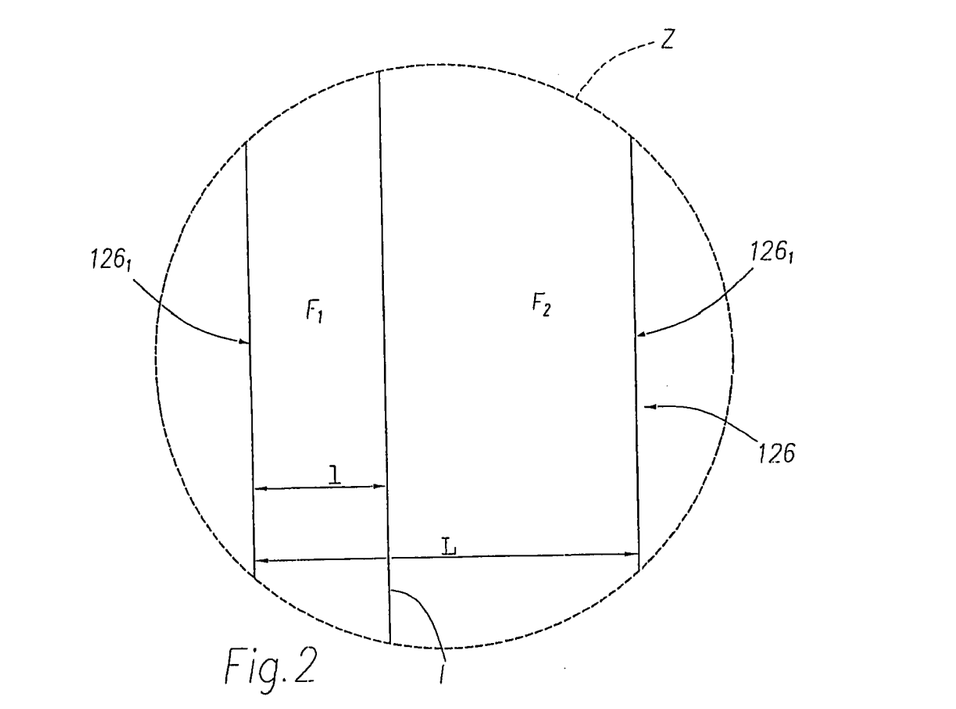
FIG. 2 is a face view on a large scale showing parallel flow of two fluids in a region of the FIG. 1 installation.

To do this, the zone Z of the microchannel 126 is viewed by means of the camera 200, as shown in FIG. 2. In FIG. 2, there can be seen a portion of the flow microchannel 126, with its walls being given the reference 126₁. The unknown and reference fluids are given respective references $F_1$ and $F_2$. Finally, the interface between these two fluids is referenced I, and it is recalled that they advance while flowing in parallel.

The method then consists in measuring the width l, of the flow of unknown fluid $F_1$. The total width of the microchannel 126 in the viewing zone Z is written L.

When the unknown fluid is Newtonian, i.e. when its viscosity is independent of the applied shear rate, use is made of the following equations.

Firstly, the main axis of the channel is written x, with y and z representing its transverse axes (see FIG. 1A). In other words, y corresponds to the width of the channel, and z to its depth, with (x, y, z) forming a rectangular frame of reference.

When a parallel flow exists, the velocity field possesses solely a component along the x axis of the channel. Under such conditions, the velocity vector is written:

$$\overline{v}_i = u_i(x,y,z)\overline{e}_x.$$

In the above equation, and in the equations below, the index i takes values 1 and 2 corresponding respectively to the unknown fluid and to the reference fluid.

Since the fluids are incompressible, equation (1) below applies:

$$\frac{\partial u}{\partial x}(x, y, z) = 0 \tag{1}$$

The Navier Stokes equations $(2_1)$, $(2_2)$, and $(2_3)$ are written as follows:

$$\frac{\partial P_i(x, y, z)}{\partial x} = \eta_i \left( \frac{\partial^2 u(y, z)}{\partial^2 y} + \frac{\partial^2 u(y, z)}{\partial^2 z} \right) \tag{2_1}$$

$$\frac{\partial P_i(x, y, z)}{\partial y} = 0 \tag{2_2}$$

$$\frac{\partial P_i(x, y, z)}{\partial z} = 0 \tag{2_3}$$

Given that the velocity field possesses solely one axial component in the x direction, it is possible to write equation (3):

$$P_i(x,y,z) = (P_{i-out}*x = P_{i-in}*(L-x))/L \tag{3}$$

In equations (2) and (3) above, $P_i$ designates the pressure for each fluid, such that the derivative of this pressure corresponds to the head loss in one of the directions x, y, or z. In addition, in equations (2), η designates viscosity.

Writing the flow rate of each fluid as $P_i$, it is possible to express this flow rate as a function of velocity using equation (4) below:

$$Q_i = c \int u_i(y,z) dy dz \tag{4}$$

It is also possible to write equation (5) relating to velocity continuity at the interface I between the two fluids:

$$u_1 = u_2 \tag{5}$$

Finally, equation (6) can be written relating to continuity of forces applied at the interface I:

$$\eta_1 \gamma_1 = \eta_2 \gamma_2 \qquad (6)$$

where $\gamma_i$ corresponds to the applied shear rate.

The six equations (1) to (6) written above belong to a system of six equations in six unknowns, that the invention proposes solving numerically.

To this end, it is necessary to begin with an acquisition stage for the computer 202, by supplying it with a large number of sextuplets ($\Delta P$, $\eta_1$, $\eta_2$, l, $Q_1$, $Q_2$), in which:

$\Delta P$ designates the pressure gradient at the location where two fluids flow in parallel;

$\eta_1$ and $\eta_2$ designate the viscosities respectively of the unknown fluid and of the reference fluid;

l designates the above-mentioned width of the flow of the unknown fluid; and $Q_1$ and $Q_2$ designate the respective flow rates of the unknown fluid and of the reference fluid.

It is also recalled that the viscosity $\eta_2$ of the reference fluid $F_2$, and the two flow rates $Q_1$ and $Q_2$ are known.

Under these conditions, by measuring the width l by means of the camera 200, it is possible to access the value of $\Delta P$, and also the viscosity $\eta_1$ of the unknown fluid, from the acquisition stage of the computer. In a variant that is not shown, it is possible to use the camera 200 to measure the width (L−l) corresponding to the flow of the reference fluid $F_2$, and then to deduce therefrom l, and subsequently $\Delta P$ and $\eta_1$.

It should be observed that under certain circumstances, the interface I shown in FIGS. 2, 4, 5A, and 5B is not vertical. Thus, for certain immiscible fluids, the flow can take the form of a jet of one fluid (unknown fluid or reference fluid) within the other (reference fluid or unknown fluid). As above, the geometrical characteristics of the flow are measured, in particular optically, and the flow is analyzed by a digital program.

When the unknown fluid is not Newtonian, i.e. when its viscosity depends on the applied shear rate, above-mentioned equations (2) are, a priori, not valid.

Under such conditions, it is necessary to associate the non-Newtonian fluid with the viscosity that a Newtonian fluid would have had under the same operating conditions, i.e. in particular, flow rates, viscosity of reference fluid, and interface position that are identical. Similarly, it is necessary to define the shear that is applied to the non-Newtonian fluid by averaging the shear rate represented by a Newtonian fluid under the same experimental conditions.

In practice, the ratio between the flow rates of the unknown fluid and of the reference fluid is decreased so that the width l of the unknown fluid in the flow microchannel 126 is reduced. Advantageously, this flow rate ratio is decreased until the width l lies in the range 5% to 20%, and in particular is close to about 10% of the total width L of the microchannel 126.

Figure 3:
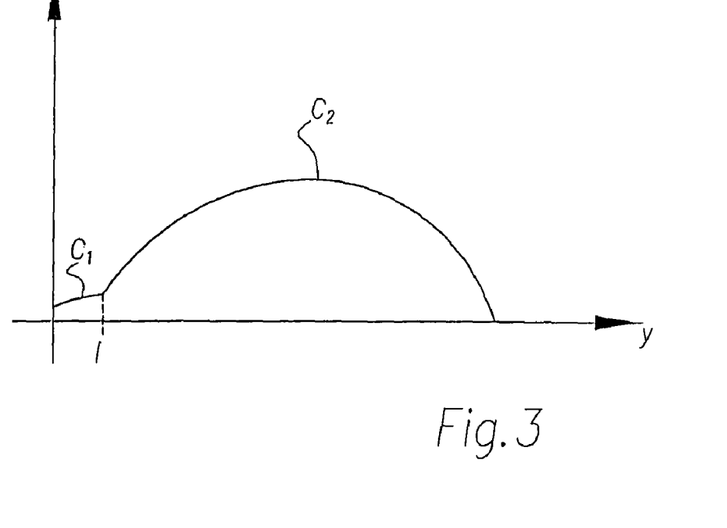
FIG. 3 is a graph showing the field of velocities of two fluids flowing in the FIG. 1 installation, while implementing a variant embodiment of the invention.

Under such conditions, the velocity profiles of the unknown and reference fluids respectively become as shown in FIG. 3. In FIG. 3, it can be seen how velocity v varies as a function of the transverse coordinate y or width of the microchannel. It can be seen that the velocity profile of the unknown fluid, represented by the portion $C_1$ to the left of the interface I, corresponds generally to a straight line, while the portion $C_2$ corresponds to the reference fluid.

This fact is equally applicable with a flow in the form of a jet, when the velocity of the unknown fluid is at least five times greater than the velocity of the reference fluid.

The slope of the velocity profile of the unknown fluid is thus substantially constant, as is the shear rate. Consequently, the viscosity $\eta_1$ of the unknown fluid, as occurs in equations ($2_1$) to ($2_3$) is likewise constant. As a result, these equations can be applied.

Figure 4:
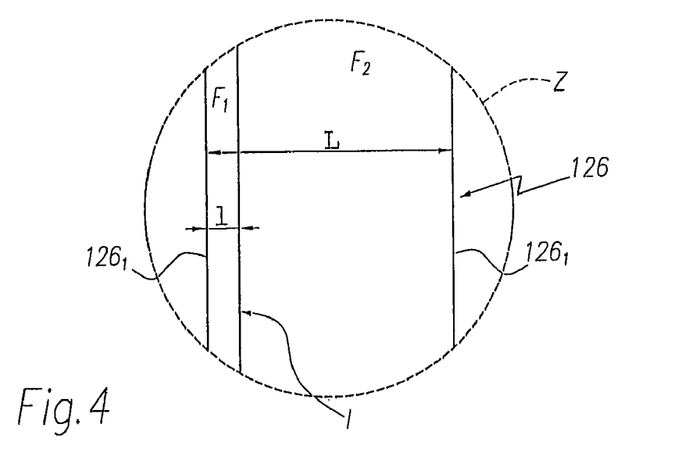
FIG. 4 is a face view on a large scale, analogous to FIG. 2, showing the flow of two fluids when implementing the variant corresponding to FIG. 3.

It is thus possible to determine the viscosity of the unknown fluid in the same manner as that explained above, for use with a fluid that is Newtonian. Thus, as shown in FIG. 4, the width l is measured accurately and arrangements are made advantageously to ensure that it is less than 20% of the total width L. Thereafter, the viscosity of the unknown fluid is deduced therefrom by applying the numerical method explained above.

A second implementation of the invention is described below for determining the characteristics of the unknown fluid. The first step is to determine the velocity fields of the two fluids along the y axis of the channel, i.e. across the width thereof. Particles are dispersed in the two fluids and the rate at which they advance is determined using the camera 200.

These particles are typically of a size lying in the range 1 μm to 4 μm, and they are constituted, for example, by beads of latex for an aqueous phase, or beads of melanin for an oil phase. These particles are easy to detect using the camera 200, given their sizes and their refractive indices.

Figure 5A:
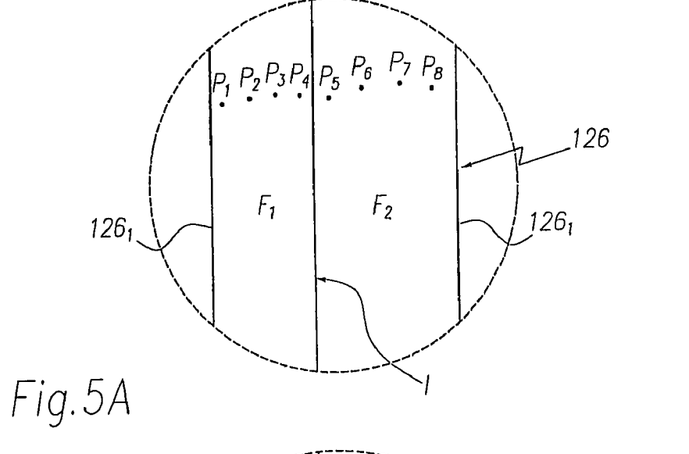
FIGS. 5A and 5B are face views on a large scale analogous to FIGS. 2 and 4 showing how the velocity fields of two fluids flowing in the installation of the invention are measured.
Figure 5B:
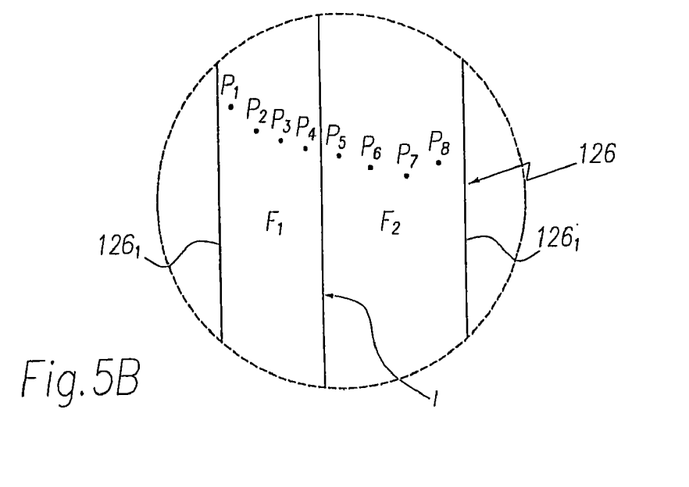

FIGS. 5A and 5B show the zone Z of the microchannel 126 in a manner analogous to that described above with reference to FIG. 2. There thus can be seen the walls $126_1$ of the microchannel 126, the unknown and reference fluids $F_1$ and $F_2$ respectively, and the interface I between these two fluids. In order to clarify the explanation, it is assumed that eight particles $P_1$ to $P_8$ have been dispersed, i.e. four particles in each fluid, it being understood that in practice the number of particles used is much greater.

FIGS. 5A and 5B correspond to different observation times, and they enable the displacement of the above-mentioned particles to be viewed. The corresponding velocities of the particles are thus equal to the ratio of the displacement distance of each particle divided by the time t between the two views. In the example shown, it can be seen that the particles $P_6$ and $P_7$ present the greatest velocities, whereas the particles $P_1$ and $P_8$ present the smallest velocities.

Figure 6:
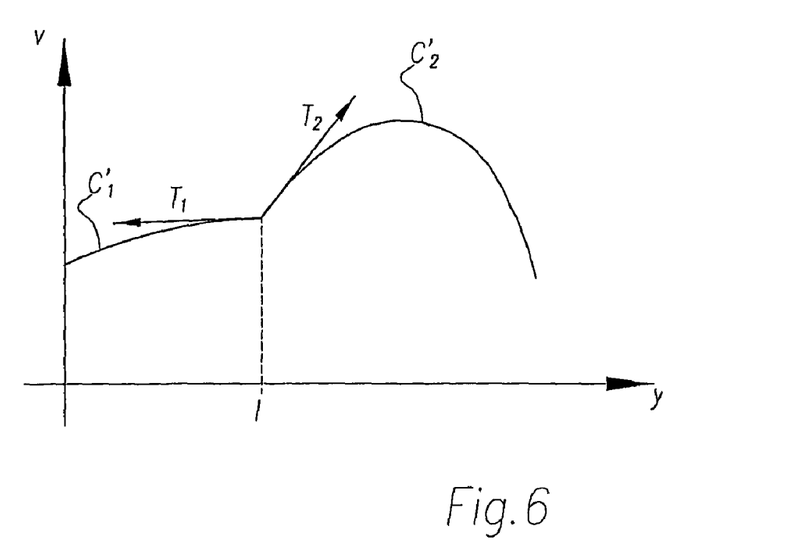
FIG. 6 is a graph analogous to FIG. 3 showing the velocity fields of two fluids, measured in the step shown in FIGS. 5A and 5B.

Under such conditions, it is possible to access the velocity profiles of the two fluids along the y axis, as shown in FIG. 6. The y coordinate is thus plotted along the abscissa with velocity $\bar{v}$ being plotted up the ordinate, and the position of the interface I can be seen. The portions $C'_1$ and $C'_2$ relate respectively to the unknown fluid $F_1$ and to the reference fluid $F_2$.

Use is then made of above-mentioned (6) relating to the continuity of the forces applied to the interface I, which equation is written as follows:

$$\eta_1 \gamma_1 = \eta_2 \gamma_2 \qquad (6)$$

As shown in FIG. 6, the tangents to the curve on either side of the interface I are determined numerically, these tangents being referenced $T_1$ and $T_2$. This gives access to the two shear rates $\gamma_1$ and $\gamma_2$, thus making it possible to deduce therefrom the viscosity $\eta_1$ of the unknown fluid, given that the viscosity $\eta_2$ of the reference fluid is known beforehand.

Both implementations described above give access to the viscosity of the unknown fluid. It should be emphasized that the invention also makes it possible to access the flow curve for the unknown fluid, in particular when the fluid is a non-Newtonian fluid, by modifying the value of the shear rate.

To do this, it is possible initially to modify at least one parameter relating to the flow of at least the unknown fluid, and where appropriate of the reference fluid. The parameter may be the flow rate, or it could be pressure. Under such conditions, increasing the flow rate gives rise to a corresponding variation in the shear rate.

Furthermore, in the second implementation, as described with reference to FIGS. 5 and 6, it is also possible to modify the location at which the velocity fields are measured. This amounts in practice to changing the value of the depth $\bar{z}$ of the channel where the measurement is taken. Thus, the closer the measurement is taken to the vicinity of the bottom of the channel, the smaller the shear rate. In contrast, on going away from the bottom of the microchannel, the shear rate tends to increase.

The invention makes it possible to achieve the above-mentioned objectives. The invention makes it possible in simple manner to determine the rheological characteristics of a fluid while using a very small quantity thereof. Furthermore, the installation of the invention requires a number of manipulations that is well below that required in the prior art as constituted by a rheometer.

Furthermore, the use of microchannels can make it very simple to vary the composition of the unknown fluid by varying the flow rates of the components of the unknown fluid. It should also be observed that the installation of the invention is generally much more compact than a rheometer, of the kind known in the state of the art.

It should also be emphasized that the invention enables in-depth knowledge to be obtained about the rheological behavior of the fluid it sets out to study. Thus, the invention makes it possible to obtain not only its viscosity, but also the curve representing the flow of said fluid. Under such conditions, the installation in accordance with the invention possess performance analogous to that of a rheometer, and much better than that of a viscometer, in particular insofar as it enables complex fluids to be studied.

The use of optical means is also advantageous. This makes the installation of the invention very simple.

Other techniques could also be used for measuring the characteristics of the interface, such as for example electrical conductivity.

Finally, making use of fluids that are respectively unknown and a reference, but that are not miscible, is also advantageous. This makes it possible to increase the accuracy of the operation of determining the rheological characteristics of the unknown fluid. In comparison, miscible fluids have a tendency to mix by diffusion, thereby falsifying viscosity measurements.

Various examples of implementing the invention are described below. These various examples relate solely to the determination device 101, without making use of the mixer device 1.

It is assumed that the microchannels 104, 106, and 126 all present a section of about 100 μm. In addition, the length of the upstream microchannels 104 and 106 is close to 4 mm, while the length of the flow microchannel 126 is about 20 mm. Finally, the junction zone 124 is conical in shape, presenting an angle at the apex of about 30°, with a cross-section S that is equal to about 400 μm at the connection with the microchannels 104 and 106.

EXAMPLE 1

The unknown fluid was glycerol, while the reference fluid was water, the experiment being carried out at 25° C. In order to plot the flow curve, the flow rate of the glycerol was varied from 1 μL/h to 10,000 μL/h, while the flow rate of the water was varied from 1 μL/h to 10,000 μL/h. For each value, the width l of the glycerol flow was measured. This gave rise to the curve reproduced in FIG. 7, which shows how stress varied as a function of shear rate.

Figure 7:
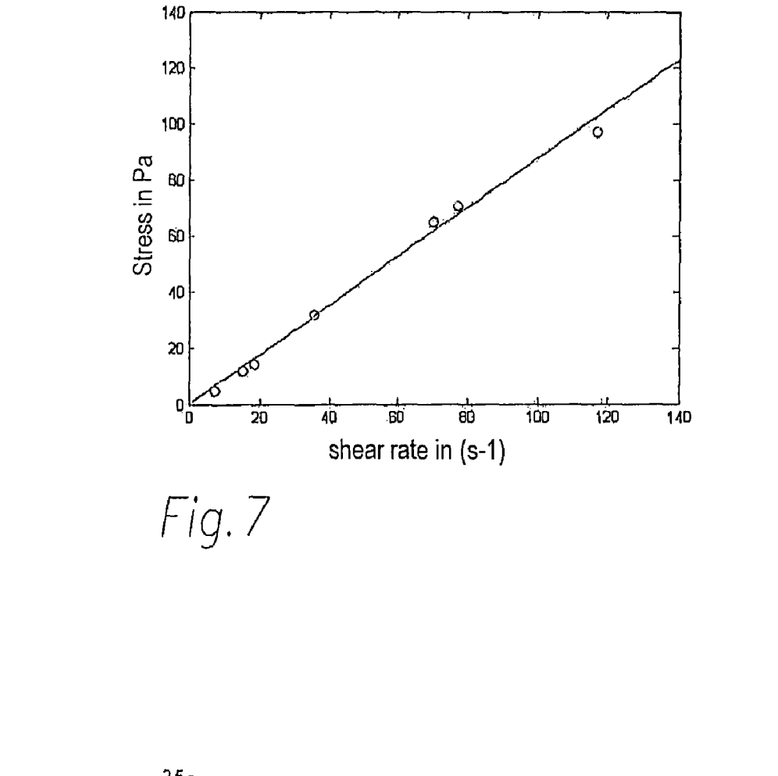
FIGS. 7 to 14 are graphs illustrating the results of Examples 1 to 8 of implementations of a method in accordance with the invention, serving to determine rheological characteristics of a fluid.

This curve serves to verify that glycerol has Newtonian behavior, i.e. stress varies linearly with shear. The gradient of this line gives the viscosity, which presents an experimental value of 877 centipoises (cP), which can be compared with the theoretical value of 890 cP, i.e. an error of less than 2%.

EXAMPLE 2

The unknown fluid was hexadecane, and the reference fluid was water. Given that those two fluids are not miscible, sodium dodecyl sulfate (SDS) was added to the water at the critical miscellar concentration. Adding this wetting agent encourages parallel flow of the water and the hexadecane.

The hexadecane was admitted into the device 101 at a rate lying in the range 1 μL/h to 10,000 μL/h, while the water was admitted at a rate lying in the range 1 μL/h to 10,000 μL/h. The position of the interface I, i.e. the width l of the hexadecane flow was measured at each flow rate value. This produced the flow curve for hexadecane at 25° C., as reproduced in FIG. 8.

Figure 8:
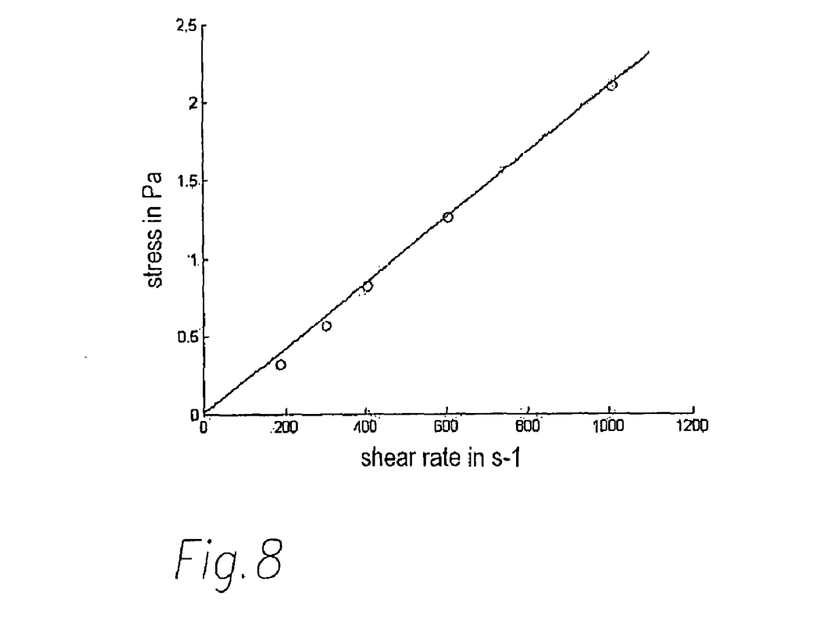

As with glycerol, the experimental curve shows in satisfactory manner that hexadecane presents Newtonian behavior. The measured viscosity was 2.1 cP, which is in good agreement with theoretical data lying in the range 2.2 cP to 2.3 cP.

EXAMPLE 3

Solutions of giant micelles were prepared, forming an unknown non-Newtonian fluid. That solution, referenced micelles 1, comprise CpCl-NaSal at 6%. Use was made of two reference fluids, constituted by silicone oil at 20 cP and at 300 cP. The corresponding experiments were carried out at an ambient temperature of 25° C.

The flow rates of micelles 1 lay in the range 120 μL/h to 10,000 μL/h, while the flow rates of the reference fluid lay in the range 1 μL/h to 10,000 μL/h. Given that the unknown fluid was non-Newtonian, precautions were taken to ensure that the width l of its flow was less than about 20% of the total width of the microchannel. The flow curve as obtained experimentally is reproduced in accompanying FIG. 9.

EXAMPLE 4

The same protocol as that implemented in Example 3 was used with micelles of CpCl-NaSal at 8%, written micelles 2. The corresponding flow curve is reproduced in accompanying FIG. 10.

Figure 9:
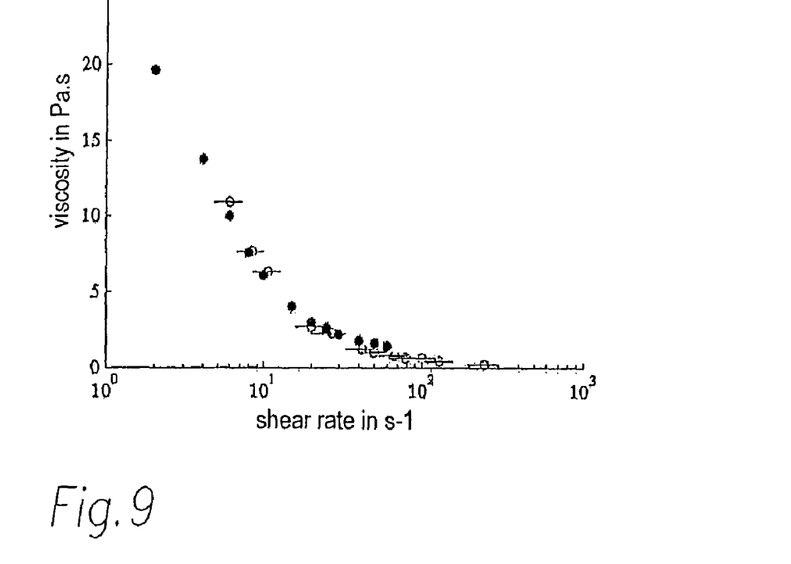
Figure 10:
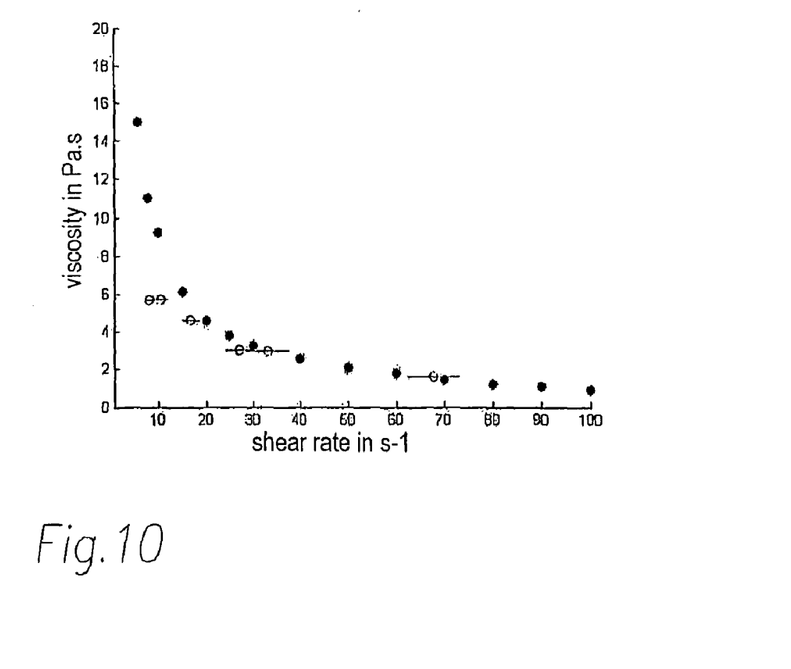

It should be observed that in the figures illustrating Examples 3 and 4, the solid symbols correspond to results obtained using a rheometer, whereas the open symbols correspond to the results obtained by implementing the installation in accordance with the invention. These two flow curves emphasize the rheofluidifying behavior of giant micelles. Furthermore, the agreement with results obtained using a conventional rheometer is satisfactory.

EXAMPLE 5

Ethylene polyoxide polymer having a molar mass of 4,000, 000 was used to prepare solutions, respectively at 4% by weight and 2% by weight. Those solutions formed an unknown non-Newtonian fluid and they were associated with a reference fluid that was 20 cP silicone oil.

Figure 11:
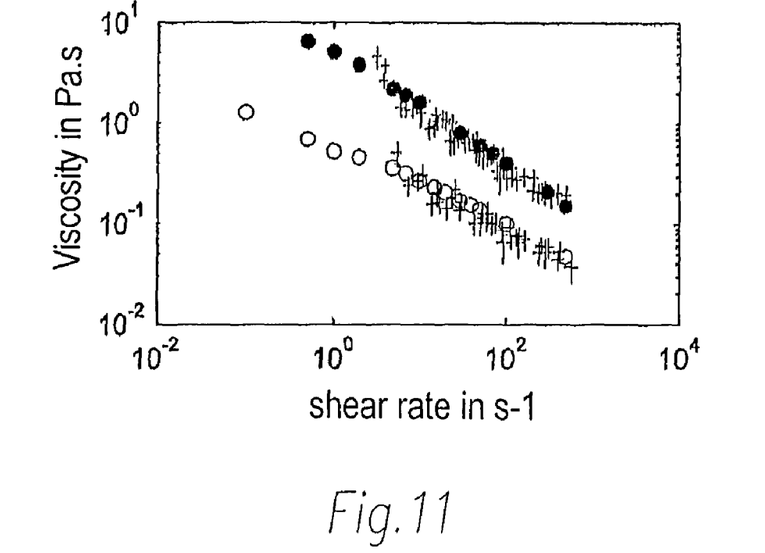

The same protocol was applied as implemented in Example 3, and the corresponding flow curves are reproduced in accompanying FIG. 11. In the figure, the various crosses correspond to measurements taken by implementing the installation in accordance with the invention, whereas the circles correspond to measurements taken using a rheometer of the state of the art. The solid circles correspond to the 4% by weight solution, while the open circles correspond to the 2% by weight solution.

In that experiment, the microchannels were etched in a PDMS plate, with a glass plate fitted thereover, as in the example described with reference to FIG. 1. The temperature was equal to 24° C.

EXAMPLE 6

The same protocol as that of Example 5 was reproduced using an unknown fluid constituted by a polydispersed emulsion of silicone oil in water, with the reference fluid being silicone with viscosity of 100 cP. In accompanying FIG. 12, the crosses correspond to results obtained by implementing the installation according to the invention, while the circles correspond to experiments performed on a commercially available rheometer.

EXAMPLE 7

The same protocol as for Example 5 was reproduced with an unknown fluid constituted by a commercial mayonnaise, together with a reference fluid constituted by a silicone oil presenting 100 cP. In accompanying FIG. 13, the crosses correspond to measurements taken by implementing the installation in accordance with the invention, analogous to that used in Examples 5 and 6, while the circles correspond to experiments performed using a commercially available rheometer.

Figure 12:
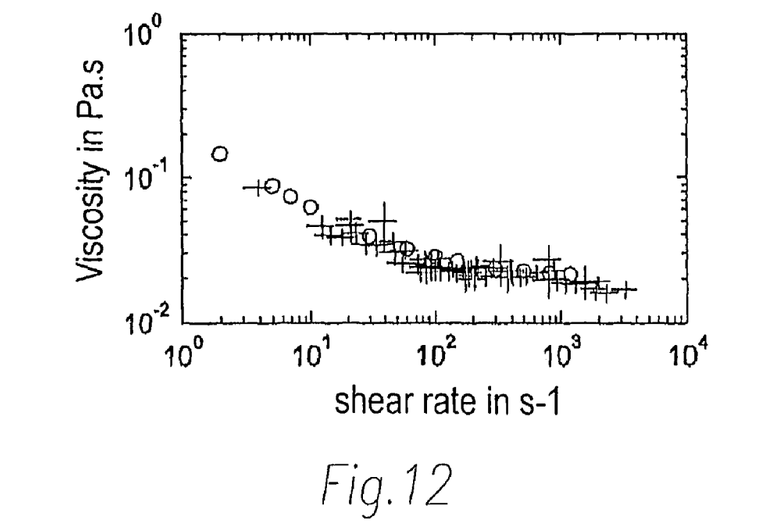
Figure 13:
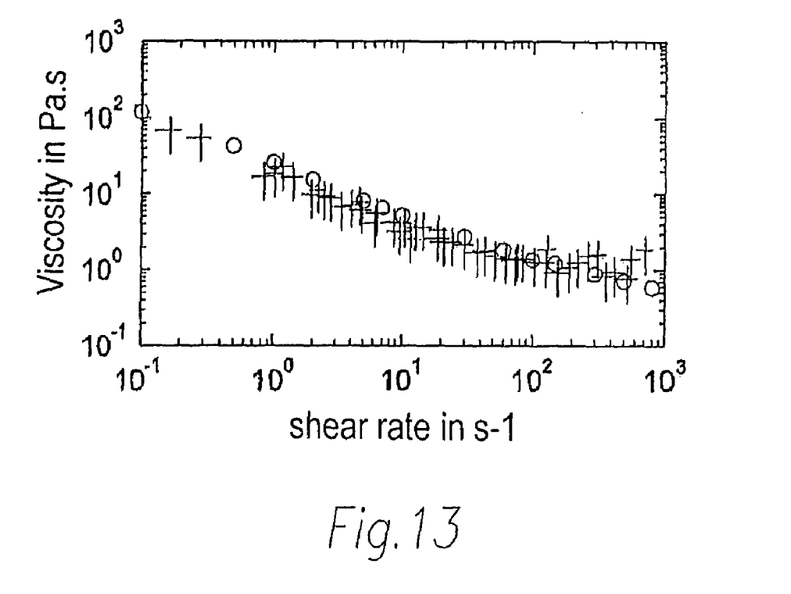

It can be seen that in FIGS. 11 to 13 showing Examples 5 to 7, there is a very satisfactory match between the results obtained with a conventional rheometer and those obtained by implementing the invention. Furthermore, these Examples 5 to 7 emphasize that the invention is applicable to fluids that are very different from one another, and that it also makes it possible to obtain viscosities and shear rates that present very small values.

EXAMPLE 8

Solutions of giant micelles were used analogous to those of Example 3, i.e. micelles 1. Use is also made of the same two reference fluids, the experiment being carried out using a protocol analogous to that of Example 3.

Compared with Example 3, the essential difference lay in the micelles having a much smaller flow rate, lying in the range 1 μL/h to 10,000 μL/h, whereas the flow rates of the reference fluid lay in the range 1 μL/h to 10,000 μL/h. This made it possible to access particularly low viscosity values and shear rates.

A series of measurements were carried out in accordance with the invention making use of another installation in accordance with the invention different from that of the above examples. In this installation, the microchannels were not etched in PDMS, but in a glass plate. It was in turn covered by another glass plate, fitted over the microchannels.

Figure 14:
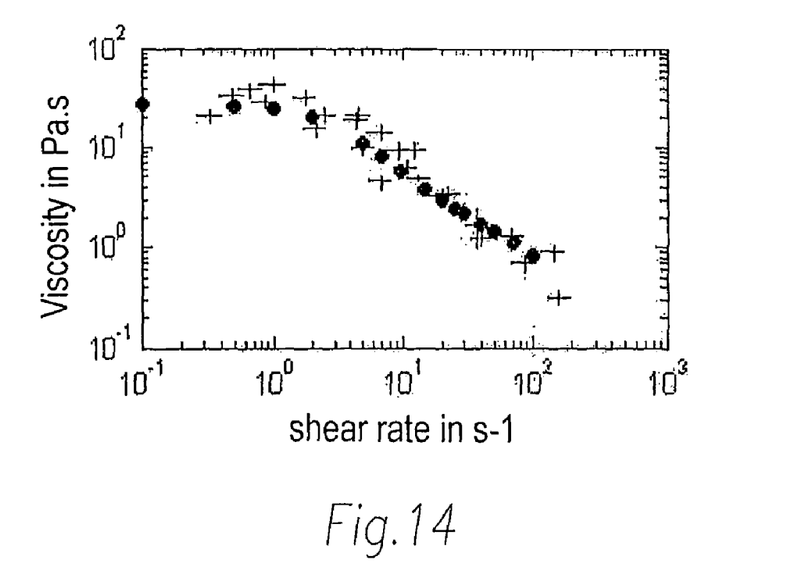

In accompanying FIG. 14, the crosses correspond to measurements performed using a state of the art rheometer, while the solid circles correspond to measurements obtained using the glass-glass plates, as described above.

It can be seen that even for very low values of shear rate, the solution making use of microchannels etched in glass is particularly advantageous, given that it matches the results obtained with a conventional rheometer in very satisfactory manner. This illustrates the fact that in order to determine the rheological characteristics of a strongly hydrophilic fluid, this solution making use of glass is particularly advantageous.

With a hydrophilic fluid, the fluid is subjected little to depletion layers in the vicinity of the glass walls, even at very slow flow rates. In other words, by using glass, there is no perceptible concentration gradient in the unknown fluid across the width of the channel, which might otherwise tend to falsify measurements. The water contained in the unknown hydrophilic fluid does not tend to stagnate in perceptible manner in the vicinity of the flow rate.

The invention claimed is:

1. A method of determining at least one rheological characteristic of an unknown fluid, the method comprising the following steps:
    causing both a reference fluid having known rheological characteristics and said unknown fluid of at least one rheological characteristic that is to be determined to flow in parallel in a flow microchannel;
    identifying the position of an interface between said two fluids in said parallel flow by measuring the width of the unknown fluid in the flow microchannel;
    determining the viscosity of said unknown fluid numerically from said measured width, by applying the following equations:

$$\frac{\partial u}{\partial x}(x, y, z) = 0 \tag{1}$$

$$\frac{\partial P_i(x, y, z)}{\partial x} = \eta_i\left(\frac{\partial^2 u(y, z)}{\partial^2 y} + \frac{\partial^2 u(y, z)}{\partial^2 z}\right) \tag{2_1}$$

$$\frac{\partial P_i(x, y, z)}{\partial y} = 0 \tag{2_2}$$

$$\frac{\partial P_i(x, y, z)}{\partial z} = 0 \tag{2_3}$$

$$P_i(x, y, z) = (P_{i-out} * x = P_{i-in} * (L-x))/L \tag{3}$$

$$Q_i = \oint u_i(y, z) dy dz \tag{4}$$

$$u_1 = u_2 \tag{5}$$

$$\eta_1 \gamma_1 = \eta_2 \gamma_2 \tag{6}$$

wherein $\eta_1$ and $\gamma_1$ represent the viscosity and the shear rate of the unknown fluid and where $\eta_2$ and $\gamma_2$ represent the viscosity and the shear rate of the reference fluid; and
    determining a curve for the flow of the unknown fluid from the viscosity, by varying the shear rate.

2. A method according to claim 1, wherein the unknown fluid is a non-Newtonian fluid and the width of said unknown fluid is kept down to a value that is less than 20% of the total width of the flow microchannel.

3. A method according to claim 2, wherein the width of said unknown fluid is kept down by increasing the ratio of the flow rates between the reference fluid and the unknown fluid.

4. A method according to claim 1, wherein the unknown fluid and the reference fluid are not miscible.

5. A method according to claim 4, wherein at least one wetting agent is added to at least one of the unknown fluid and the reference fluid in order to avoid drops forming in the parallel flow.

6. The method according to claim 5, wherein the at least one wetting agent is added to at least the reference fluid.

7. A method according to claim 1, wherein the unknown fluid is a mixture of at least two components, and said at least two components are mixed together prior to causing the unknown fluid to flow in parallel with the reference fluid.

8. A method according to claim 7, wherein said at least two components are introduced into a mixer microchannel etched in a material suitable for absorbing a mixer gas, and said mixer gas is introduced into said mixer microchannel.

9. A method according to claim 8, wherein the mixer microchannel is etched in poly(dimethylsiloxane), and the mixer gas is air.

10. A method of identifying chemical compounds, associations of chemical compounds, or compositions, the method comprising the following steps:
   a) preparing at least two different compounds, associations, or compositions;
   b) measuring at least one rheological characteristic by the method in accordance with claim 1; and
   c) identifying a compound, association, or composition presenting a rheological property.

11. A method according to claim 10, wherein the compounds, associations, or compositions are liquid compounds, associations, or compositions for coatings, fluids for gas or oil deposits, for phytosanitary compositions, for care of the skin or the hair, for home care or for detergent compositions for hard surfaces.

12. The method according to claim 1, wherein identifying the position of the interface comprises a step of viewing the interface and its vicinity.

13. An installation for implementing a method of determining at least one rheological characteristic of an unknown fluid, the installation comprising a device for determining at least one rheological characteristic of the unknown fluid, the determination device comprising:
   a body in the form of a plate;
   a flow microchannel formed in the body and suitable for receiving the parallel flow of the unknown fluid and of the reference fluid;
   means for introducing said two fluids into the flow microchannel;
   means for identifying at least one item of data representative of the interface between said two fluids in the parallel flow; and
   means for determining the at least one rheological characteristic of the unknown fluid, from the or each identified data item.

14. An installation according to claim 13, wherein the means for introducing the two fluids comprise first and second upstream microchannels opening out into the flow microchannel.

15. An installation according to claim 14, wherein the two upstream microchannels are connected to the flow microchannel via a junction zone of section that decreases going towards the flow microchannel.

16. The installation according to claim 15, wherein the junction zone comprises a funnel shape.

17. An installation according to claim 14, wherein the determination means comprise a computer.

18. An installation according to claim 13, further comprising a mixer device comprising:
   a body in the form of a plate, made of a material that is suitable for absorbing a mixer gas;
   feed means for feeding components for forming the unknown fluid;
   a mixer microchannel for mixing said components;
   feed means for feeding said mixer gas into the mixer microchannel; and
   an outlet put into communication with the means for introducing the unknown fluid into the flow microchannel.

19. An installation according to claim 18, wherein the component feed means comprise microchannels for feeding the components that open out into the mixer microchannel.

20. An installation according to claim 18, wherein the mixer gas feed means comprise a microchannel for feeding said gas that opens out into the mixer microchannel.

21. An installation according to claim 18, wherein the mixer microchannel is provided with bends enabling shocks to be created in the component mixer, in order to make them homogenous.

22. An installation according to claim 18, wherein the body of the mixer device and/or the body of the determination device is/are made of poly(dimethylsiloxane).

23. An installation according to claim 18, wherein the mixer gas is air.

24. An installation according to claim 18, wherein the body of the mixer device and the body of the determination device are separate.

25. An installation according to claim 18, wherein the cross-section of the flow microchannel, and/or of the upstream microchannels, and/or of the mixer microchannel, and/or of the component feed microchannels, and/or of the mixer gas feed microchannel lies in the range 20 µm to 500 µm.

26. The installation according to claim 25, wherein the cross-section of the flow microchannel, and/or of the upstream microchannels, and/or of the mixer microchannel, and/or of the component feed microchannels, and/or of the mixer gas feed microchannel is in the range of 50 µm to 200 µm.

27. An installation according to claim 13, wherein the flow microchannel is bordered by walls made of glass.

28. The method of identifying chemical compounds, associations of chemical compounds, or compositions, the method comprising the following steps:
   a) preparing at least two different compounds, associations, or compositions;
   b) measuring at least one rheological characteristic using the installation in accordance with claim 13; and
   c) identifying a compound, association, or composition presenting a rheological property.

29. The installation according to claim 13, wherein the identification means comprise a camera.

30. A method of determining rheological characteristics of an unknown fluid, the method comprising:
   causing both a reference fluid having known rheological characteristics and said unknown fluid of rheological characteristics that are to be determined to flow in parallel in a flow microchannel;
   identifying velocity fields of the two fluids on either side of an interface between said two fluids in said parallel flow, by measuring the velocities of particles dispersed in said fluids;
   determining the viscosity of the unknown fluid by applying an equation for stress field continuity at the interface, $\eta_1 \gamma_1 = \eta_2 \gamma_2$, where $\eta_1$ and $\gamma_1$ represent the viscosity and the shear rate of the unknown fluid and where $\eta_2$ and $\gamma_2$ represent the viscosity and the shear rate of the reference fluid; and
   determining a curve for the flow of the unknown fluid from the viscosity, by varying the shear rate.

31. A method according to claim 30, wherein at least one parameter of at least the flow of the unknown fluid is modified in order to cause the shear rate to vary.

32. A method according to claim 31, wherein the places at which the velocity fields of the two fluids are identified are modified in order to vary the shear rate.

33. The method according to claim 31, wherein the at least one parameter of at least the flow of the unknown fluid that is modified in order to cause the shear rate to vary, includes the flow rate or the pressure.

* * * * *